United States Patent [19]

Bean et al.

[11] Patent Number: 5,432,059
[45] Date of Patent: Jul. 11, 1995

[54] ASSAY FOR GLYCOSYLATION DEFICIENCY DISORDERS

[75] Inventors: Pamela Bean, Los Angeles; Jeff W. Terryberry, Santa Monica, both of Calif.

[73] Assignee: Specialty Laboratories, Inc., Santa Monica, Calif.

[21] Appl. No.: 222,422

[22] Filed: Apr. 1, 1994

[51] Int. Cl.[6] ............... C12Q 1/48; C12Q 1/54; C12N 9/10; G01N 21/64
[52] U.S. Cl. ............................ 435/15; 435/14; 435/193; 436/87; 436/164; 436/172; 436/800; 436/811; 530/395; 530/400; 530/829; 530/830
[58] Field of Search ............... 435/15, 193, 14; 436/800, 805, 164, 172, 87, 88, 811; 530/829, 830, 400, 395

[56] References Cited

PUBLICATIONS

Ashwell et al. "Carbohydrate-Specific Receptors of the Liver" Ann Rev. Biochem. 51: 531-533 1982.
Stibler "Carbohydrate-Deficient Transferrin in Serum: A New Marker of Potentially Harmful Alcohol Consumption Reviewed" Clin Chem 37(12): 2029-2037 1991.
Stibler, et al. "Glycoprotein Glycosyltransferase Activites in Serum in Alcohol-Abusing Patients & Healty Controls" Scand. J. Clin Lab Invest. 51(1) 43-51 1991.
Anton et al. "Two Methods for Measuring Carbohydrate-Deficient Transferrin in Inpatient Alcoholics & Healthy Controls Compared" Clin Chem. 40(3) 364-368 Mar. 1994.

*Primary Examiner*—Michael G. Wityshyn
*Assistant Examiner*—Nancy J. Degen
*Attorney, Agent, or Firm*—Harris F. Brotman; Gray Cary Ware & Freidenrich

[57] ABSTRACT

A method is provided for detecting carbohydrate-deficient glycoproteins in samples taken from subjects with metabolic disorders, such as alcohol abuse and subjects who display a syndrome of carrying abnormal levels of carbohydrate deficient glycoproteins. The method involves steps of reglycosylating with a fluorescent-conjugate deglycosylated glycoproteins in a sample of body fluid from a subject. A further step involves fluorometric detection of fluoresceinylated carbohydrates incorporated into truncated serum glycoproteins.

34 Claims, 4 Drawing Sheets

ASSAY FOR GLYCOSYLATION DEFICIENCY DISORDERS

FIELD OF THE INVENTION

This invention relates to the application of a method for detecting carbohydrate-deficient glycoproteins (CDG) in a subject. More particularly, the invention involves a method for detecting and quantitating carbohydrate-deficient glycoproteins in fluid samples obtained from subjects with metabolic disorders, typically arising from alcohol abuse or congenital defects in protein glycosylation.

DESCRIPTION OF THE RELATED ART

The magnitude of alcohol-related problems in the United States alone is enormous. Approximately 18 million Americans are considered to be alcohol dependent. Currently, over 200,000 deaths per year (1 of every 10 deaths) are attributable to alcoholism. Twenty percent of total medical expenditures in the U.S. for hospital care are alcohol-related (West et al. Ann. Int. Med., 100:405–416, 1984). In the United States, the annual cost of lost productivity and health care expenses related to alcoholism is estimated to be $117 billion (Sixth Special Report to Congress on Alcohol and Health, Rockville, Md., Dept. Health and Human Services, NIAAA, 1987, p. 21–23 (DHHS Publ. No. ADM 87-1519)).

Current tests used to diagnose alcohol abuse are not specific for the condition. Hence, multiple tests are performed and evaluated to arrive at a diagnosis of alcohol abuse. Severity indices based on multiple tests are used to monitor treatment of alcohol-related liver disease (Blake et al. Clin Chem 37:5–13, 1991). In alcohol abuse, the serum gamma-glutamyl transferase is often elevated (Rollason et al. Clin Chim Acta 39:41–47 (1972)). Alpha lipoprotein (Johannson et al. Acta Med Scand 195:273–277 (1974)) and serum iron (Hillman, R. Ann N.Y. Acad Sci 275:297–306 (1975); Herbert et al. Ann N.Y. Acad Sci 252:307–315 (1975)) concentrations can also be elevated.

The level of alcohol intake is an important predictor of treatment outcome (Blake et al. Clin Chem 37:5–13 (1991); Orrego et al. N Engl J Med.317:1421–1427, 1987). However, patients, especially alcohol abusers, are unreliable in reporting alcohol consumption (Orrego et al. Lancet pp. 1354–1356, 1979). Thus, a biochemical test which correlates with prolonged, excessive alcohol consumption, i.e., level of alcohol intake, would be very useful for prognostic purposes and hence in planning and monitoring treatment.

It is known that higher isoelectric point isoforms of transferrin are elevated in 81% of patients who ingest at least 60 grams of ethanol daily for a week or more. (Stibler. Clin Chem 37:2029–2037, 1991). Transferrin is a protein that transports iron into cells and is present at high concentrations in serum. The higher isoelectric point isoforms represent carbohydrate-deficient transferrins (CDT), presumably resulting from interruption of glycosyltransferase-mediated glycosylation of glycoproteins or elevated sialidase activity in serum. These isoforms (CDT) return to normal if the patient abstains from alcohol consumption for 10 days or more (Stibler et al. Acta Med Scand 206:275–281, 1979). Other studies have shown that the higher concentrations of aberrant transferrins in alcohol abusers are independent of previous or associated liver disorders, i.e., non-alcoholic liver disease patients do not exhibit the elevations of carbohydrate-deficient transferrin, except in a few cases of primary biliary cirrhosis. Determination of increased CDT concentrations may provide early, objective evidence of alcohol abuse in women in early stages of pregnancy and thus, the risk of fetal alcohol syndrome (Stibler et al. Alcoholism: Clin Ex Res 11:468–473, 1987; Stibler et al. Alcohol 5:393–398, 1988 ).

Although biochemical tests for decreased glycosyltransferase activity would be useful, assays for such enzyme activities in serum or other body fluids involve troublesome and difficult procedures and/or isolation of the product, i.e., reglycosylated proteins. Among other difficulties, such assays typically involve the use of radioactive ligands, entailing additional safety precautions and disposal problems. (Stibler et al. Scand J Clin Lab Invest 51:43–51, 1991).

SUMMARY OF THE INVENTION

In accordance with the present invention, a method is provided which overcomes the above-mentioned problems and furnishes a single specific test which largely replaces multiple non-specific tests commonly employed for detecting prolonged high alcohol consumption and which allows detection of other metabolic disorders associated with aberrant forms of glycoproteins. The present method detects carbohydrate-deficient glycoproteins in a subject, and, in particular, a subject with one or more metabolic disorders. The method involves the steps of obtaining a sample of body fluid from a subject, the sample containing carbohydrate-deficient glycoprotein. The carbohydrate-deficient glycoprotein is reglycosylated with a fluorescent monosaccharide analog, and the fluorescent reglycosylated glycoprotein is detected in a fluorometer. A further step involves quantitating the amount of reglycosylated glycoprotein in serum, body fluids or other tissues by extrapolation from a standard curve.

The above-discussed and many other features and attendant advantages of the present invention will become better understood by reference to the following detailed description of the invention when taken in conjunction with the accompanying drawings.

DETAILED DESCRIPTION OF THE INVENTION

Figure 1:
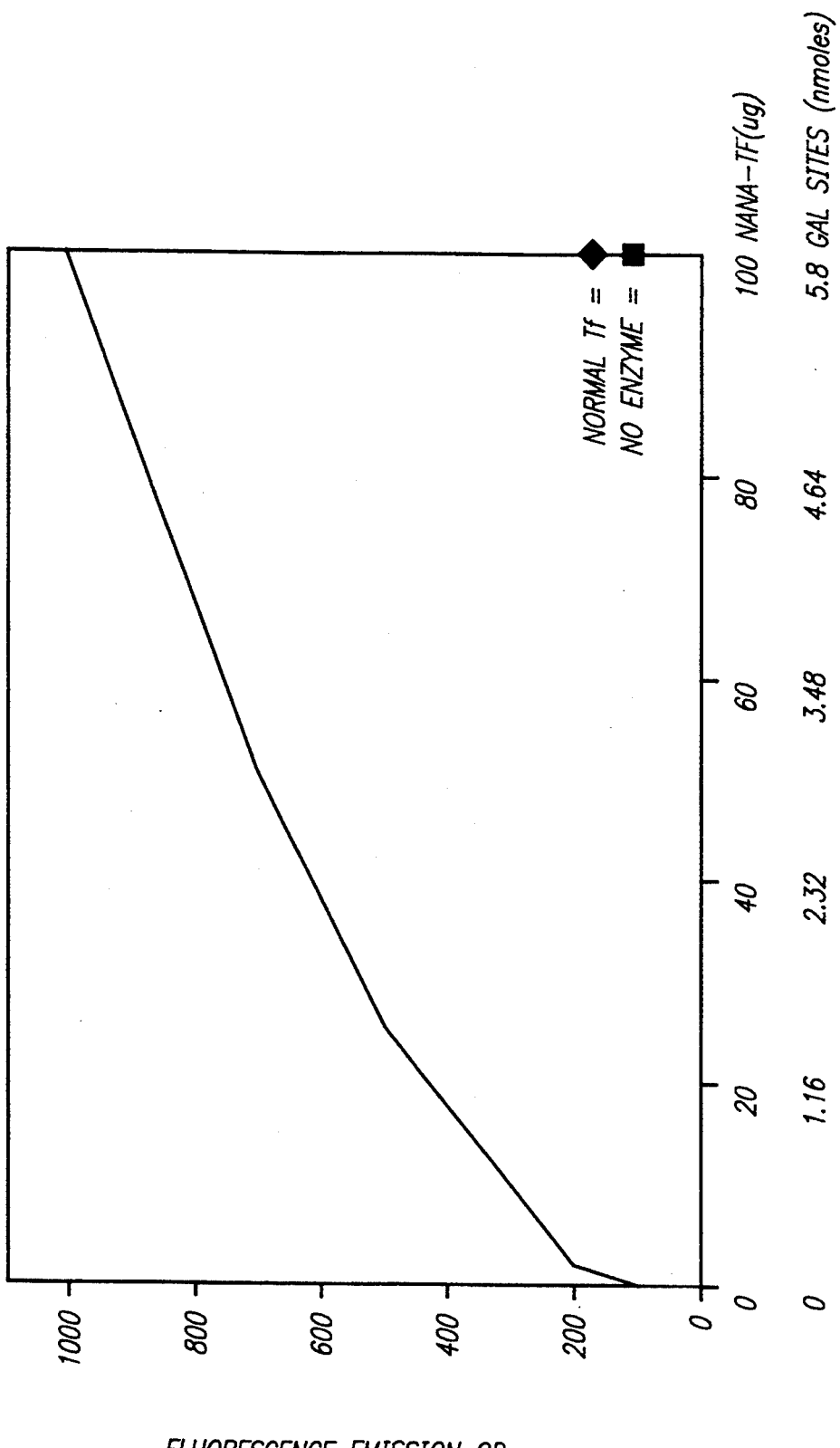
FIG. 1 shows a standard curve indicating increased incorporation of the fluorescent donor with increasing concentrations of the acceptor (neuraminidase-treated transferrin).

The present invention provides a method for detecting carbohydrate-deficient glycoproteins in a subject. Certain advantages are provided by the method of the present invention for identifying alcohol abuse in subjects. In particular, the present method, based on detecting carbohydrate-deficient glycoproteins in a sample taken from a subject, is useful for detecting a species of carbohydrate-deficient glycoproteins associated with alcohol abuse. The method of the invention also provides an assay for detecting carbohydrate-deficient glycoproteins in samples taken from subjects with other metabolic disorders, as set forth below.

The method of the invention relies on detection of an enzyme-generated fluorescent product by an assay which detects carbohydrate-deficient glycoproteins in samples of body fluids obtained from subjects with metabolic disorders. In the present method, the sample of body fluid, which contains carbohydrate-deficient glycoproteins, is contacted or mixed with a combination of glycosylation enzymes plus appropriate fluorescently labeled nucleotide sugars so as to incorporate fluoresceinylated carbohydrates (typically monosaccharides) in carbohydrate-deficient (or deglycosylated) glycoproteins and, in particular, serum glycoproteins.

For detecting the metabolic disorder associated with alcohol abuse, the method of the invention relies on the presence of an elevated concentration of higher isoelectric point (pI) isoforms of transferrin in 81% of subjects who ingest at least 60 grams of ethanol daily for a week or more (Stibler et al. Acta Med Scand 206:275-281, 1979). These subjects are referred to herein as "abusers." Non-abusers are referred to herein as "normal consumers." The elevated concentrations of higher isoelectric point isoforms of transferrin (CDT) characteristically return to normal if the subject abstains from alcohol consumption for 10 days or more. Thus, the method of the invention is used clinically for detecting and quantitating carbohydrate-deficient glycoproteins and carbohydrate-deficient transferrin, which probably arise, among other possibilities, from aberrant glyosyltransferase and glycosidase concentrations due to hepatic injury in patients who abuse alcohol (Stibler. Clin Chem 37:2029-2037, 1991; Bean et al. Alcoholism: Clin Exp Res 17:11653-1170, 1993; Stibler et al. Scand J Clin Lab Invest 51:43-51, 1991; Malagolini et al. J Am Clin and Exper Res 13(5):649, 1989).

The vast majority of the plasma proteins circulate as glycosylated proteins (glycoproteins), which are simply proteins with covalently attached carbohydrate side chains. The oligosaccharide groups of glycoproteins (sometimes known as side chains), which are linked enzymatically to the core polypeptide during the normal course of its biosynthesis, are composed of several different monosaccharides; these carbohydrate side chains are usually branched. Attachment of side chains to the protein involves either an N-glycosidic or an O-glycosidic bond, and four different linkages occur in proteins of mammalian origin. The most prevalent linkage, the N-linkage involving asparagine (Asn) and N-acetyl-D-glucosamine (GlcNAc), is present in most of the plasma glycoproteins as well as in many cell surface glycoproteins (Martinez et al. Lab Invest 57:240-257, 1987).

In contrast to the biosynthesis of O-linked glycoproteins, N-linked glycoproteins are not synthesized by the simple step-wise addition of sugars to a protein. Rather, individual monosaccharides are first assembled into a high-mannose structure on a carrier lipid and the entire structure is then transferred in a single step to the peptide. The lipid, which is known as dolichol-phosphate (dolichol-P), is an unsaturated fatty acid containing 80 to 110 carbons and belonging to the polyprenol family. The glucosylated high-mannose structure, which is N-glycosidically linked in a single step to an asparagine moiety of the polypeptide, constitutes the precursor for oligosaccharide processing and the addition of peripheral sugars to the outer chain structure.

The trimming of monosaccharides and the addition of peripheral sugars is an orderly process that is mediated by glycosidases and transferases present in the endoplasmic reticulum and Golgi apparatus.

The final peripheral sugars which are generally added during ologosaccharide synthesis are sialic acid (SA) and/or fucose (Fuc). Linkage of SA can generally influence the physico-chemical and biologic properties of glycoproteins (Martinez et al. Lab Invest 57: 240-257, 1987).

The structure of the sugar chain is determined by the high specificity of the glycosyltransferases recognizing proteins/glycoproteins as acceptor products and sugar-nucleotides as substrates. These enzymes also form specific types of glycosidic linkages ($\alpha$ or $\beta$) and transfer given monosaccharides specifically to a carbon of the growing protein-linked acceptor sugar. The completed glycoproteins are packaged into secretory vesicles in the Golgi apparatus and transferred to the blood after fusion of these vesicles with the cell membrane. (Molnar. Moll Cell Biochem; 6:3-14, 1975).

Transferrin (Tf) is a monomeric glycoprotein with the property of transporting iron from the digestive tract to cells in the body via the bloodstream. The carbohydrate structure of human transferrin consists of two N-linked oligosaccharides with structural variation due to differences in branching and outer chain structure. The main isoform circulating in the blood is a complex type oligosaccharide containing two branches (biantennary) of galactose and N-acetyl glycosamine bound to the processed high-mannose core with four terminal sialic acids.

Alterations in the electrophoretic mobility of transferrin have been described in association with alcohol abuse. Disturbances of the Golgi-associated glycosylation pathway in liver are associated with consumption of more than 60 g of alcohol per day ($\sim$ 1 bottle of wine) for seven to ten consecutive days; these disturbances result in elevated concentrations of carbohydrate-deficient transferrin isoforms which contain two, one and no sialic acid residues in contrast to the usual four sialic acid residues. In fact, CDT is the best available marker for the diagnosis of alcohol abuse because of its high specificity ($>90\%$) and sensitivity (70%) (Anton et al. Clin Chem 40:364-368, 1994).

The two major methods developed for CDT quantitation are isoelectric focusing/immunoblotting with quantitation by laser densitometry (IEF/IB/LD), and microcolumn anion-exchange chromatography with quantitation by radio-immunoassay (MAEC-RIA). Both methods allow distinction of CDT from normal Tf isoforms because of differences in charge due to the lack of sialic acid residues (de Jong et al. Int J Biochem; 21:253-263, 1989; Anton et al. Clin Chem 40:365-368, 1994). Carbohydrate-deficient transferrin isoforms may involve transferrins lacking galactose and N-acetyl-glucosamine as well (Stibler et al. Alcoholism: Clin Exp Res 10:61-64, 1986).

A recently described, very sensitive fluorometric assay for $\alpha 2,6$ sialyltransferase activity is based on the transfer of 5-acetamido-9-deoxy-9-fluoroesceinylthioureiodoneuraminic acid onto distinct glycoproteins. The kinetic properties of the enzyme were not affected by the fluoresceinyl residue on the substrate. Fluorescence bound to acceptor protein was quantified after gel filtration which separated fluorescent sialoglycoprotein from free fluorescence-labeled cytidine monophosphateglycoside donor. Employing very small amounts of donor, acceptor and enzyme, the method was used to determine the kinetic properties of purified rat liver α2,6-sialyltransferase reacting with four separate glycoprotein acceptors differing in glycan structure (Gross et al. Analyt Biochem 186:127–134, 1990; Gross et al. Eur J Biochem 177: 583–589, 1988).

The method of the present invention, which involves detecting carbohydrate-deficient glycoproteins in human body fluids, is achieved with the following steps. A sample of body fluid is obtained from a subject. The sample, which might contain carbohydrate-deficient glycoprotein, is typically a serum sample, but could also be plasma or other body fluid or tissue. The serum sample is typically not processed before mixing the serum with enzyme and donor, but pretreatment or processing in a variety of ways is also possible.

As set forth in the Examples below, a sample of serum obtained from a subject and containing carbohydrate-deficient glycoprotein is contacted or mixed with one or more glycosylation enzymes and a nucleotide monosaccharide-fluorescent conjugate. Glycosylation enzymes which find utility in the present invention include, but are not limited to glycosyltransferases. Preferred glycosylation enzymes are sialyltransferases and galactosyltransferases.

A typical embodiment of the present method uses sialyltransferase to reglycosylate (e.g., resialate), carbohydrate-deficient transferrin, i.e., a carbohydrate-deficient glycoprotein produced in various metabolic disorders and serving as a diagnostic marker of these disorders.

The step of reglycosylation is achieved by mixing the serum sample, glycosylation enzymes, e.g. glycosyltransferase, and nucleotide carbohydrate fluorescent conjugate under conditions sufficient to reglycosylate, i.e., incorporate fluoresceinylated monosaccharides into some or all of the carbohydrate-deficient glycoproteins. Nucleotide carbohydrate fluorescent conjugates which are useful in the present method include, but are not limited to 9-fluoresceinyl-NeuAc-cytidine monophosphate. Another nucleotide carbohydrate which can be used to increase fluorescent incorporation is unlabeled β-D-galactose-uridine diphosphate.

Typical reaction conditions involve mixing from about 2 μL to about 20 μL of serum (preferably about 10 μL of serum) with 0.5–2.0 mU of α2,6 sialyltransferase and 0.4–4.0 μM fluoresceinyl-Neu-Ac-CMP in a 50–200 μL final reaction volume. Reaction buffer is 50.0–62.5 mM sodium cacodylate, pH 6.5, 0.01% Triton X-100. Incubation is for 0.5–2 hours at 35°–37° C., followed by precipitation of proteins with 1 mL of cold 1% phosphotungstic acid in 0.5M hydrochloric acid. After centrifugation at 9500 rpm for 20 seconds, the pellet is washed twice in 1 mL of cold methanol. After the final wash, the pellet is resuspended in 1 mL of 50 mM NaCl with 20 μL of 1 N NaOH. pH is adjusted to 7–8 with 1N HCl and fluorescence emission is read at 515 nm ($OD_{515}$) using an excitation filter of 490 nm.

When the reglycosylation step is completed, the reglycosylated glycoprotein is detected. The step of detecting comprises measuring the fluorescence emission from the reglycosylated glycoprotein. Typically, the reaction mixture resulting from the reglycosylation step is placed in a fluorometer, such as one manufactured by Sequoia-Turner Corporation, Mountain View, Calif. 94073, Model 450 Digital, and fluorescence emission measured at 515 nm ($OD_{515}$). Alternatively, the reaction mixture can be incubated in antigen capture enzyme immunoassay (EIA) and read in a microplate fluorometer at similar wavelengths. The fluorescence detected indicates the reglycosylation of the carbohydrate-deficient glycoprotein in the sample. The amount of reglycosylated protein produced in the reglycosylating step is quantified as the amount of fluorescence incorporated into the carbohydrate-deficient glycoprotein by reference to a standard curve and reported as nanomoles of galactose acceptor sites/mg of protein. Thus, through a process of regalactosylation and resialylation using cold uridine-diphosphate-galactose and fluoresceinylated cytidine monophosphate-sialic acid, CDT and CDGs can be quantified for diagnostic purposes.

EXAMPLES

1. Preparation of Sialic Acid-Free Transferrin (TF): Acceptor Substrate

Neuraminidase bound to sepharose beads (300 μl, 130 mU, Sigma Chemicals) is washed twice with 1.5 mL sodium acetate buffer, 20 mM, while rotating for 10 minutes at room temperature, followed by centrifugation at 9500 g for 20 seconds. The supernatant is discarded and 150 μL of human apo-transferrin, 20 mg/mL, plus 800 μL of sodium acetate buffer, 20 mM, pH 5.0 is added to the pellet of beads. The mixture is incubated overnight at room temperature on a rocker. The supernatant containing sialic acid-free transferrin is transferred to a new tube and the volume is adjusted to 1 mL with diluent C (20 mM sodium acetate, 50 mg/mL aprotinin, 100 mg/mL thimerosal). 100 μL aliquots are stored at −20° C. for up to six months.

2. Incorporation of CMP-9-Fluoresceinyl Sialic Acid (9-CMP-AcNeu) into Neuraminidase-Treated Transferrin: Standard Curve for Quantification of Reglycosylation Increasing concentrations of neuraminidase-treated Tf are incubated with a constant amount of exogenous sialyltransferase (1 mU, Boehringer Mannheim) and cytidine-5′-monophospho-9-(3-fluoresceinylthioureido)-9-deoxy-N-acetylneuraminic acid (CMP-9-fluoresceinyl-AcNeu; 0.4 nM, Boehringer Mannheim) for 60 minutes at 37° C. After precipitation with phosphotungstic acid, extraction with methanol and pH adjustment, fluorescence emission at 515 nm ($OD_{515}$) is measured. The standard curve (FIG. 1) indicates increased incorporation of the fluorescent donor with increasing concentrations of neuraminidase-treated transferrin. The presence of normal Tf or the absence of enzyme in the assay results in background fluorescence.

3. Incorporation of CMP-9-Fluoresceinyl Sialic Acid into Affinity-Purified Transferrin Derived From Normal Consumers and Alcohol Abusers Affinity Chromatography: Tf-specific antibodies (Tago Immunologicals, Burlingame, Calif.) coupled to sepharose 4B gel (Pharmacia) are prepared according to the manufacturer's specifications. For the preparation of purified Tf from serum, 3 mL of gel are mixed with 1 mL of serum for 30 minutes at room temperature (RT). The mixture is washed twice each with 0.2M phosphate buffered saline (PBS), pH 7.2 and 2M KI. Purified Tf is eluted with 0.1M glycine-HCl, pH 2.3; the eluate is neutralized with 1.0M NaOH. After overnight dialysis against $H_2O$ at 4° C., the purified Tf is concentrated by lyophilization.

Figure 2:
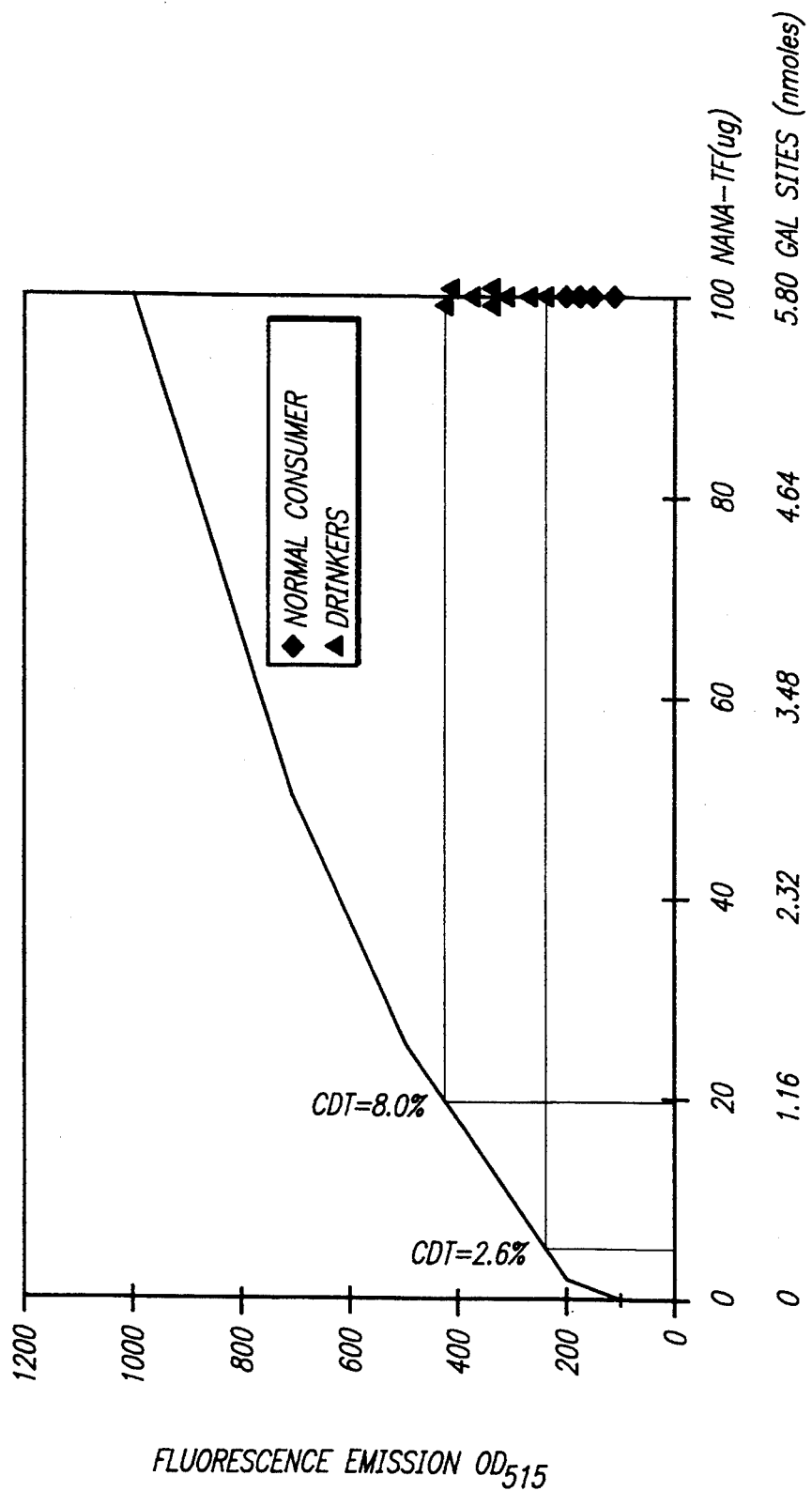
FIG. 2 shows incorporation of CMP-9-fluoresceinyl sialic acid into affinity-purified transferrin derived from normal consumers and alcohol abusers.

Steady state fluorescent emission of affinity purified Tf (250 μg) is elevated in eight alcohol abusers (250–410 $OD_{515}$), compared to four control donors whose alcohol intake is less than 15 g/day (138–180 $OD_{515}$) (FIG. 2). Likewise, the average concentration of galactose (gal) acceptor sites, based on a standard curve using neuraminidase-treated Tf, is elevated among alcohol abusers (1.015 nmoles) compared to control donors (0.174 nmoles). As shown in FIG. 2, these concentrations, representing 2.6% and 8% carbohydrate-deficient Tf (CDT) of total Tf, correlate well with previously reported values (Stibler et al. Alcoholism: Clin Exp Res 10:535–544, 1986; Xin et al. Alcoholism: Clin Exp Res 15:814–821, 1991).

Figure 3:
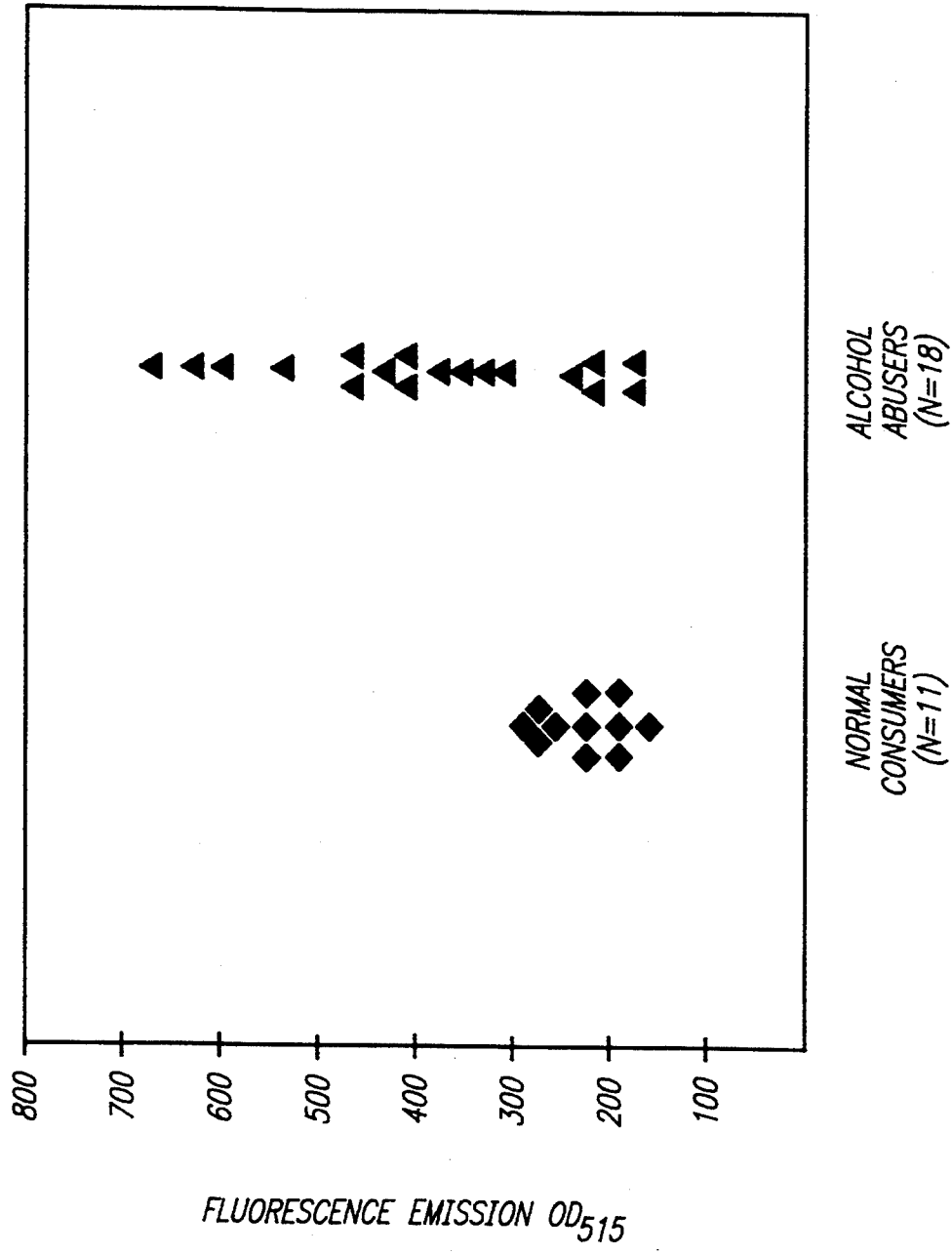
FIG. 3 shows incorporation of CMP-9 fluoresceinyl sialic acid into sera derived from normal consumers and alcohol abusers.

4. Incorporation of CMP-9 fluoresceinyl Sialic Acid into Sera Derived from Normal Consumers and Alcohol Abusers FIG. 3 illustrates that uptake of 9-CMP-AcNeu into glycoproteins in 20 μL samples of serum obtained from subjects (less background activity of endogenous enzyme on endogenous acceptors) ranged from 168–682 $OD_{515}$ among 18 alcohol abusers, and from 169 to 278 $OD_{515}$ for 11 control donors. Thirteen of the 18 alcohol abuser samples measured greater than 300 $OD_{515}$, equivalent to 0.87 galactose acceptor sites, whereas 11 control donor samples measured less than the 300 $OD_{515}$ cut off. Concentration of galactose acceptor sites in serum glycoproteins of the alcohol abusers and control donors ranged from 0.115–2.73 nmoles and 0.116–0.725 nmoles, respectively. Sera samples from two alcohol abusers who had abstained from alcohol for more than four weeks averaged values of 199 and 225 $OD_{515}$, resembling the values obtained for the control specimens.

Figure 4:
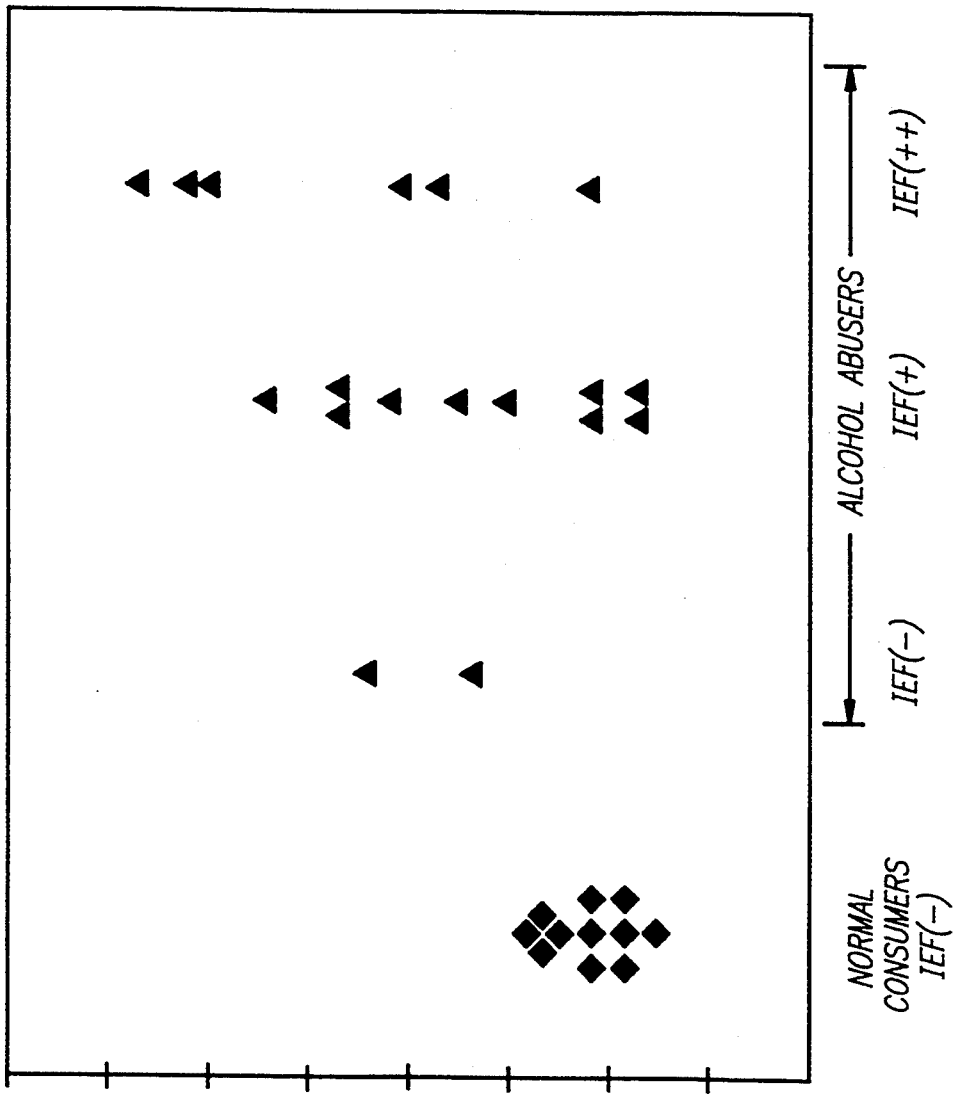
FIG. 4 shows fluorescence emission compared to isoelectric focusing/immunoblotting in sera derived from normal consumers and alcohol abusers.

5. Fluorescence Emission Compared to Isoelectric Focusing/Immunoblotting Pattern in Sera Derived From Normal Consumers and Alcohol Abusers When compared to isoelectric focusing/immunoblotting (IEF/IB), a well accepted technique for CDT diagnosis, 11 of 18 alcohol abusers tested positive in both assays, two were positive by the fluorometric assay of the present invention but negative by IEF/IB, and five were negative by the fluorometric assay, but positive by IEF/IB (FIG. 4). All control donors, as well as the two abstinent alcohol abusers, were negative in both assays. These results indicate that resialylation of a portion of the carbohydrate-deficient glycoprotein using the method of the present invention involving enzyme-catalyzed coupling of fluorescent sialic acid to oligosaccharide chains of serum glycoproteins is accurate, rapid and useful for the diagnosis of alcohol abuse.

The clinical utility and reliability of the application of this method finds support in showing that higher CDT concentrations in alcohol abusers are independent of previous or associated liver disorders, i.e., non-alcoholic liver disease patients do not exhibit high CDT concentrations (Stibler et al. Alcoholism: Clin Exp Res 11:468–473, 1987; Stibler et al. Alcohol 5:393–398, 1988). Accordingly, determination of CDT concentrations by the method of the present invention also is useful for furnishing early, objective evidence of alcohol abuse in men or women, even after initial blood alcohol levels return to normal.

Glycoproteins other than transferrin can also have altered patterns of glycosylation in alcohol abusers (Ghosh et al. Alcoholism: Clin Exp Res 17:576–579, 1993; Guasch et al. Alcoholism: Clin Exp Res 16:942–948, 1992). Accordingly, the method of the present invention can be extended to include detection of any or all these other carbohydrate-deficient glycoproteins. As explained below, the method of the present invention also finds utility in detecting and quantitating transferrin and glycoprotein homologs in subjects with genetic syndromes characterized by carbohydrate-deficient serum glycoproteins.

It is well understood by those skilled in the art that deficiencies in protein glycosylation are associated with alcohol abuse, carbohydrate-deficient glycoprotein syndromes (CDGS), hereditary erythroblastic multinuclearity (HEMPAS), lysosomal storage diseases and other pathologies (Stibler et al. Arch of Dis in Childhood 65:107–111, 1990; Yamashita et al. J Biol Chem 268(8):5783–5789, 1993; Fukuda et al. Brit J Haem 82:745–752, 1992; Hillmen et al. Proc Nat Acad Sci USA, 90:5272–5276, 1993). Accordingly, the method of the present invention finds use in detecting CDGs associated with these metabolic disorders and finds use as well in detecting generalized, localized, specific and non-specific defects of glycosylation including, but not limited to all serum glycoproteins or other specific acceptors, e.g., fetuin, alpha$_1$-acid glycoprotein, erythrocyte glycoproteins. The enzymatic cascade responsible for the formation of complex-type oligosaccharides is altered by drugs, congenital defects, alcoholism, and certain infections (Stibler et al. Arch of Dis in Childhood 65:107–111, 1990; Yamashita et al. J Biol Chem 268(8):5783–5789, 1993; Fukuda et al. Brit J Haem 82:745–752, 1992) and may also be useful for such investigations. In addition, the regulation of glycosidase levels or activities in various disease states can lead to elevated concentrations of CDGs (Richards in *Biochemistry of the Glycosidic Linkage*, R. Piras, ed., Academic Press, 1972, p. 207; Dedonder, R. ibid, pg. 21). CDT is a well established biochemical marker in alcohol abuse, as well as CDGS and HEMPAS. Accordingly, the method of the present invention finds utility for diagnosis of metabolic disorders based on specific detection of a variety of incompletely glycosylated glycoproteins in the circulation, associated with a variety of metabolic disorders. For example, using α(2,6)-sialyltransferase and 9-fluoresceinyl-neuraminic acid-cytidine monophosphate, desialylated CDT/CDG can be resialylated and the fluorescence incorporation quantified using a fluorometer. Degalactosylated glycoproteins can also be detected by sequential addition of β(1,4) galactosyltransferase and unlabeled UDP-galactose, to produce a galactosylated glycoprotein. This is sequentially followed by contacting the galactosylated glycoprotein with a mixture comprising another glycosylation enzyme and a nucleotide monosaccharide-fluorescent conjugate under conditions sufficient to incorporate fluoresceinylated carbohydrate into a portion of the galactosylated glycoprotein. The second mixture is typically the resialation mixture described above. The sensitivity of the present method for detecting CDT increases when using the sequential product protocol, i.e., galactosylation followed by sialylation. Two of the four alcohol abusers who tested negative when using sialyltransferase alone became positive when using the sequential assay for an overall clinical sensitivity of 83% for diagnosis of sustained alcohol abuse.

The method of the present invention would find further use in detecting a genetic syndrome in children characterized by a severe neurologic deficit and high concentrations of carbohydrate-deficient glycoproteins including CDT (about 25% of total transferrin) (Stibler et al. Arch Dis Childhood 65:107–111, 1990; Jaeken et al. *Genetics of Neuropsychiatric Diseases,* Wetterburg, L. ed., Wenner-Gren Int. Symp. Series, vol. 51, MacMillan Press, London, pp. 69–80, 1989; Kristiansson et al. Arch Dis Childhood 64:71–76, 1989; Jaeken et al. Clin Chim Acta 144:245–247, 1984).

Having thus described exemplary embodiments of the present invention, it should be noted by those skilled in the art that the disclosures herein are exemplary only and that various other alternatives, adaptations and modifications may be made within the scope of the present invention. Accordingly, the present invention is not limited by the specific embodiments as illustrated herein but is only limited by the following claims.

What is claimed is:

1. A method for detecting carbohydrate-deficient glycoproteins in a subject with a metabolic disorder, said method comprising the steps of:
    (a) obtaining a sample of body fluid from a subject, said sample comprising deglycosylated glycoprotein;
    (b) reglycosylating with a fluorescent-labeled conjugate a portion of said deglycosylated glycoprotein;
    (c) detecting the reglycosylated glycoprotein made in step (b).

2. The method of claim 1 wherein said step of detecting comprises quantitating the amount of reglycosylated glycoprotein.

3. The method of claim 1 wherein said sample of body fluid is serum.

4. The method of claim 1 wherein said reglycosylating comprises contacting said sample with a mixture comprising a glycosylation enzyme and said fluorescent-labeled conjugate under conditions sufficient to incorporate the fluorescent label into a portion of said deglycosylated glycoprotein, wherein said fluorescent-labeled conjugate is a nucleotide carbohydrate-fluorescent conjugate.

5. The method of claim 4 wherein said glycosylation enzyme is a glycosyltransferase.

6. The method of claim 4 wherein said nucleotide carbohydrate-fluorescent conjugate is a fluorescent CMP-glycoside.

7. The method of claim 4 wherein said nucleotide carbohydrate-fluorescent conjugate is CMP-9-Fluoresceinyl-AcNeu.

8. The method of claim 1 wherein said reglycosylating comprises the steps of
    (a) contacting said sample with a first mixture comprising a first glycosylation enzyme and a first nucleotide-sugar conjugate to produce a first reglycosylated glycoprotein; and
    (b) contacting the first reglycosylated glycoprotein with a second mixture comprising a second glycosylation enzyme and a nucleotide carbohydrate-fluorescent conjugate under conditions sufficient to incorporate fluoresceinylated carbohydrate into a portion of said first reglycosylated glycoprotein.

9. The method of claim 8 wherein said first nucleotide-sugar conjugate is an unlabelled UDP-glycoside.

10. The method of claim 9 wherein said first nucleotide-sugar conjugate is UDP-galactose.

11. The method of claim 8 wherein said first and second glycosylation enzymes are glycosyltransferases.

12. The method of claim 11 wherein said first glycosylation enzyme is galactosyltransferase.

13. The method of claim 11 wherein said second glycosylation enzyme is sialyltransferase.

14. The method of claim 8 wherein said nucleotide carbohydrate-fluorescent conjugate is a fluorescent CMP-glycoside.

15. The method of claim 8 wherein said nucleotide carbohydrate-fluorescent conjugate is CMP-9-Fluoresceinyl-AcNeu.

16. A method for diagnosing a metabolic disorder in a subject, said method comprising the steps of:
    (a) obtaining a sample of body fluid from a subject, said sample comprising deglycosylated glycoprotein;
    (b) reglycosylating with a fluorescent-labeled conjugate a portion of said deglycosylated glycoprotein to produce a reglycosylated glycoprotein;
    (c) quantitating the reglycosylated glycoprotein made in step (b);
    (d) comparing the amount of reglycosylated glycoprotein quantitated in step (c) to the amount of reglycosylated glycoprotein in samples of body fluid from normal subjects and subjects known to have said metabolic disorder.

17. The method of claim 16 wherein said sample of body fluid is serum.

18. The method of claim 16 wherein said reglycosylating comprises contacting said sample with a mixture comprising a glycosylation enzyme and said fluorescent-labeled conjugate under conditions sufficient to incorporate the fluorescent label into a portion of said deglycosylated glycoprotein, wherein said fluorescent-labeled conjugate is a nucleotide carbohydrate-fluorescent conjugate.

19. The method of claim 18 wherein said glycosylation enzyme is a glycosyltransferase.

20. The method of claim 19 wherein said glycosylation enzyme is sialyltransferase.

21. The method of claim 18 wherein said nucleotide carbohydrate-fluorescent conjugate is a fluorescent CMP-glycoside.

22. The method of claim 18 wherein said nucleotide carbohydrate-fluorescent conjugate is CMP-9-Fluoresceinyl-AcNeu.

23. The method of claim 16 wherein said reglycosylating comprises the steps of
    (a) contacting said sample with a first mixture comprising a first glycosylation enzyme and a first nucleotide-sugar conjugate to produce a first reglycosylated glycoprotein; and
    (b) contacting the first reglycosylated glycoprotein with a second mixture comprising a second glycosylation enzyme and a nucleotide carbohydrate-fluorescent conjugate under conditions sufficient to incorporate fluoresceinylated carbohydrate into a portion of said first reglycosylated glycoprotein.

24. The method of claim 23 wherein said first and second glycosylation enzymes are glycosyltransferases.

25. The method of claim 24 wherein said first glycosylation enzyme is galactosyltransferase.

26. The method of claim 24 wherein said second glycosylation enzyme is sialyltransferase.

27. The method of claim 23 wherein said first nucleotide-sugar conjugate is an unlabelled UDP-glycoside.

28. The method of claim 27 wherein said first nucleotide-sugar conjugate is UDP-galactose.

29. The method of claim 23 wherein said nucleotide carbohydrate-fluorescent conjugate is a fluorescent CMP-glycoside.

30. The method of claim 23 wherein said nucleotide carbohydrate-fluorescent conjugate is CMP-9-Fluoresceinyl-AcNeu.

31. The method of claim 16 wherein the step of quantitating comprises measuring fluorescence emission from said reglycosylated glycoprotein.

32. The method of claim 16 wherein said metabolic disorder is alcoholism.

33. The method of claim 16 wherein said deglycosylated glycoprotein is transferrin.

34. The method of claim 16 wherein said metabolic disorder is a carbohydrate-deficient glycoprotein syndrome.

* * * * *